(12) United States Patent
Jensen et al.

(10) Patent No.: US 11,100,621 B2
(45) Date of Patent: Aug. 24, 2021

(54) SIMULATED POST-CONTRAST T1-WEIGHTED MAGNETIC RESONANCE IMAGING

(71) Applicant: Imaging Biometrics, LLC, Elm Grove, WI (US)

(72) Inventors: Todd R. Jensen, Brookfield, WI (US); Jay F Urbain, Mequon, WI (US)

(73) Assignee: Imaging Biometrics, LLC, Elm Grove, WI (US)

( * ) Notice: Subject to any disclaimer, the term of this patent is extended or adjusted under 35 U.S.C. 154(b) by 0 days.

(21) Appl. No.: 16/164,966

(22) Filed: Oct. 19, 2018

(65) Prior Publication Data

US 2019/0122348 A1  Apr. 25, 2019

Related U.S. Application Data

(60) Provisional application No. 62/575,048, filed on Oct. 20, 2017.

(51) Int. Cl.
| | |
|---|---|
| *G06K 9/00* | (2006.01) |
| *G06T 5/00* | (2006.01) |
| *G06T 7/00* | (2017.01) |
| *G16H 50/50* | (2018.01) |
| *G06T 11/00* | (2006.01) |

(52) U.S. Cl.
CPC ............ *G06T 5/009* (2013.01); *G06T 7/0016* (2013.01); *G06T 11/00* (2013.01); *G16H 50/50* (2018.01); *G06T 2207/10088* (2013.01); *G06T 2207/20081* (2013.01); *G06T 2207/20084* (2013.01); *G06T 2207/20208* (2013.01); *G06T 2207/30004* (2013.01); *G06T 2207/30016* (2013.01)

(58) Field of Classification Search
None
See application file for complete search history.

(56) References Cited

U.S. PATENT DOCUMENTS

2019/0108634 A1\* 4/2019 Zaharchuk ............. G06N 3/084

\* cited by examiner

*Primary Examiner* — Sean M Conner
(74) *Attorney, Agent, or Firm* — Glenn H. Lenzen; Elevated IP, LLC

(57) ABSTRACT

A system and method for generating simulated post-contrast T1-weighted magnetic resonance (MR) images without the use of exogenous contrast material based upon patient-specific non-contrast MR images using machine learning/artificial intelligence techniques to train the system to generate post-contrast T1-weighted magnetic resonance images based upon retrospectively collected non-contrast MR images of various sequence types including T1-weighted, T2-weighted, FLAIR (Fluid-Attenuated Inversion Recovery), and/or DWI (Diffusion-Weighted Imaging).

9 Claims, 3 Drawing Sheets

SIMULATED POST-CONTRAST T1-WEIGHTED MAGNETIC RESONANCE IMAGING

CROSS-REFERENCE TO RELATED APPLICATIONS

This application claims priority to U.S. Provisional Patent Application Ser. No. 62/575,048 filed on Oct. 20, 2017.

FIELD OF THE INVENTION

The present invention relates generally to magnetic resonant imaging (MRI). More specifically, the present invention relates to systems and non-invasive MRI methodologies that provide clearly-defined tissue contrast in MRI images without the use of contrast agents.

BACKGROUND OF THE INVENTION

Magnetic resonance imaging (MRI) relies on the relaxation properties of excited hydrogen nuclei in water and lipids to create images. When the target object to be imaged is placed in a uniform magnetic field, the forces in the magnetic field cause the spins of atomic nuclei having a non-zero spin to align in a particular manner with the applied magnetic field. By way of example, hydrogen atoms have a simple spin (½) and therefore align either parallel or anti-parallel to the magnetic field. A radio frequency pulse (RF) is then applied in a direction perpendicular to the magnetic field and removed. When the RF signal is removed, the atomic nuclei relax. During the relaxation process, the nuclei release energy by emitting an RF signal unique to the nuclei, which may be measured by a conductive field coil placed around the target object. This measurement is processed or reconstructed to obtain the magnetic resonance images.

The signal intensity of a given tissue type depends upon the density of the protons in the tissue. However, the contrast of the image also depends on two other tissue-specific parameters: the longitudinal relaxation time (T1) and the transverse relaxation time (T2). T1 defines the time required for the displaced nuclei to return to equilibrium, that is to say, the time required for the nuclei to realign themselves in the magnetic field. T2 is the time required for the signal emitted by a specific tissue type to decay, or, stated differently, a time constant for the decay of the transverse magnetization arising from the transversely-application RF pulse. A third parameter T2* relaxation defines the decay of transverse magnetization arising from natural interactions at the atomic or molecules levels within the tissue of interest and from magnetic field in homogeneities, T2* is always less than or equal to T2.

Image contrast is created by using a selection of image acquisition parameters that weights signals by T1, T2 or T2*, or no relaxation time, which are known in the art as proton density images. For example, in the brain, T1-weighting causes the nerve connections of white matter to appear white, and the congregation of neurons of gray matter to appear gray. Cerebrospinal fluid appears dark.

Injected contrast agents may be used to further enhance tissue contrast in MRI images by inducing changes in the T1 relaxation or T2/T2* relaxation of tissue water. Most commonly, a paramagnetic contrast agent, typically a gadolinium compound is employed for this purpose; although, as will be discussed in greater detail below, several different contrast agents may also be used. For example, gadolinium-enhanced tissues and fluids appear extremely bright in T1-weighted images, thereby providing high contrast sensitivity which facilitates the detection of vascular tissues (tumors).

It is estimated that 50% of all magnetic resonance imaging (MRI) and magnetic resonance angiography (MRA) rely on the use of an exogenous contrast material or agent, with gadolinium-based contrast agents (CAs) being the most common. As noted above, CAs are administered intravenously and when subjected to a magnetic field, enhance the diagnostic quality of MRI scans by improving their sensitivity and/or specificity. MRI contrast injections improve diagnostic accuracy in some conditions, such as inflammatory and infectious diseases of the brain, spine, soft tissues and bones, by making images clearer so that the radiologist can better see what and where problems exist. The nature and extent of some cancers and benign tumors are best seen and assessed after an injection of CA. Also, scans showing the function of blood vessels in real time can be carried out using CAs and many heart abnormalities can only be fully assessed as well.

By definition, MR imaging is meant to be a non-invasive procedure. In 1983, Peter Lauterbur, et al, demonstrated the benefits of using paramagnetic CAs intravenously to improve tissue discrimination. Since then, CAs have become indispensable in diagnostic imaging procedures, as they provide clarity for clinicians when making diagnostic decisions. The invasive injection of CAs are, for the most part, safe with very low risk of adverse side effects. Although minor, risks do exist. Below are some common and relatively recently discovered risks associated with the use of CAs:

Nephrogenic Systemic Fibrosis

Nephrogenic systemic fibrosis (NSF) is a rare debilitating disease resulting in skin contractures (or localized skin thickening and tightening) and internal organ damage. It has occurred with some gadolinium-based contrast media in a minority of patients with pre-existing severe kidney function abnormalities. Some forms of gadolinium contrast media exist that create lower risks of NSF than other forms. These low-risk forms are used in patients with less severe renal disease if the likely benefit (better diagnosis) justifies the very low likelihood of subsequent NSF. Even for those patients with end-stage kidney disease, the risk of NSF developing after a single injection of a lower risk agent is believed to be well under 1 in 100 injections.

Gadolinium Retention

Recently, it has been recognized that very small amounts of at least some forms of gadolinium contrast (about 1% of the injected dose) are retained in the tissues, mostly in the bones, with tiny amounts in the brain. Retention seems to be more likely with the same forms of gadolinium contrast that have a higher risk for NSF. No adverse effects are believed to be caused by these very small amounts of retained gadolinium. However, radiologists, as a cautionary measure, recommend the use of gadolinium contrast only where it is likely to assist the diagnosis.

Allergy-Like Reactions

Less frequently than the foregoing, in approximately 1 in 1000 patients, an itchy skin rash has been observed within a few minutes of the injection. The rash is believed to be the result of a mild allergic reaction to the CA and usually settles down by itself within an hour or so. Its appearance should be monitored closely as a potential precursor to a more serious allergic reaction.

Workflow and Procedural Related Issues

Proper injection/administration of the CA requires additional patient time (not to mention slight discomfort) and, if not injected properly, results in wasted CA material, inefficient use of resources (hospital personnel), and wasted MR scanner time. In these situations, rescheduling the patient and performing another scan may be required to achieve an accurate diagnosis.

Financially, the global CA market is estimated to reach USD 5.44 Billion by 2021. In the USA alone, there were an estimated 39 million MR procedures performed in 2016. This equates to 19.5 million MR procedures that used CAs. Conservatively, if each dose of CA costs $100, the direct material expense alone equates to roughly $2 billion. This does not include the indirect costs associated with operational The use of Machine Learning (ML and associated tools are increasing in applications across a variety of fields and disciplines, including the MRI field). Although prior work by the inventor of the subject invention and collaborators has shown the utility of ML for identifying areas of future contrast enhancement, this work relied on the use of imaging with exogenous contrasts agents. See, Jensen T. R. "*Detection of Brain Tumor Invasion Within Edema Using Multiparametric Imaging and Computational Intelligence*", PhD Dissertation, Department of Biomedical Engineering, Marquette University/Department of Biophysics, Medical College of Wisconsin, May, 2006; and Jensen T. R. and Schmainda K. M., "*Computer-Aided Detection of Brain Tumor Invasion Using Multiparametric MRI*", JMRI, 30(3) 481-489, 2009.

Synthetic MR has developed a product to generate synthetic MR images with different contrast from the images collected using a specific acquisition sequence (basically a combined T1- and T2-mapping sequence). In this case, the contrast is the endogenous contrast between different tissue types for only pre-contrast images (or post-contrast if the acquisition was performed after exogenous contrast injection). The Bloch equations for MR are solved to find the intrinsic T1, T2, and proton density (PD) values for each pixel. Then, using these values, the synthetic MR images can be generated using the same equations and adjusting echo time (TE), repetition time (RT), and other acquisition variables. However, this approach does not offer a method to identify the effects of exogenous contrast without the use of exogenous contrast. This product is licensed to or marketed by major MR vendors including GE Healthcare (MAGiC), Philips Healthcare (SyntAC), and Siemens Healthineers. Olea Medical, a Toshiba Medical company, also offers a similar product referred to as Computated MRI which use Bayesian techniques to generate the synthetic MR images.

In view of the foregoing, a need exists for an MRI procedure which eliminates the use of contrast agents and their associated health risks, streamlines clinical workflows, reduces procedure costs related to contrast agent and contrast agent administration, and conserves clinical resources (labor and equipment), yet still produces the sharp, clearly defined tissue contrast required for precise medical diagnosis and treatment.

SUMMARY OF THE INVENTION

The present invention is based on Machine Learning (ML) and Deep Learning techniques using only non-contrast MR images as inputs. These inputs include T1-weighted, T2-weighted, fluid attenuation inverse recovery (FLAIR), and/or diffusion weighted-imaging (DWI) sequences.

In an embodiment, a collection of retrospectively collected inputs and the post-contrast T1+C as the target output as used to generate the simulated T1+C image.

In another embodiment, an image analogous to post-contrast (T1+C) image is generated without the use of an exogenous CA is automatically generated within a few seconds and eliminates common operational and procedural errors plaguing current clinical practice.

These and other features, aspects and advantages of the present invention will become apparent to those skilled in the art from the following detailed description, which, taken in conjunction with the accompanying drawings, discloses a preferred embodiment of the present invention.

BRIEF DESCRIPTION OF THE DRAWINGS

Referring now to the attached drawings which form a part of the original disclosure.

DESCRIPTION OF THE PREFERRED EMBODIMENT

Selected embodiments of the present invention will now be explained with reference to the figures and flow diagrams. It will be apparent to those skilled in the art from this disclosure that the following descriptions of the embodiments of the present invention are provided for illustration only and not for the purpose of limiting the invention as defined by the appended claims and their equivalents.

The visual information in MR images of brain lesions is provided by the change in tissue relaxivity due to the accumulation of contrast agent (CA) material in extravascular tissues caused by a permeable ("leaky") blood-brain barrier arising from tumor angiogenesis or other disease processes. This information may also be available from a combination of anatomical and functional imaging performed prior to any introduction of exogenous CA. Machine learning is a field of artificial intelligence (AI) which uses statistical methods to impart to computer systems the ability to learn from data, identify patterns and make decisions without human intervention or explicit programming. The novel methodology of the instant invention utilizes machine learning technology to train and test a model to output a simulated post-contrast T1-weighted image using information available from a set of retrospectively acquired MRI images. More specifically, pre-contrast images are used as inputs to generate post-contrast images as the target output. The trained model is then used to generate simulated post-contrast T1-weighted images using only pre-contrast images as input without injecting CA into the patient.

As will be described in greater detail below, the method of the present invention uses a novel system and combination of image and data processing technology, DICOM formatting (Digital Imaging and Communications in Medicine), artificial intelligence (AI) and machine learning/artificial intelligence as noted above to process selected inputs, which were obtained without the use of contrast agent, from which it generates T1+C images for the treatment of various conditions without the use of potentially harmful contrast agents. The inputs may or may not undergo a calibration or normalization preprocessing step.

Figure 1:
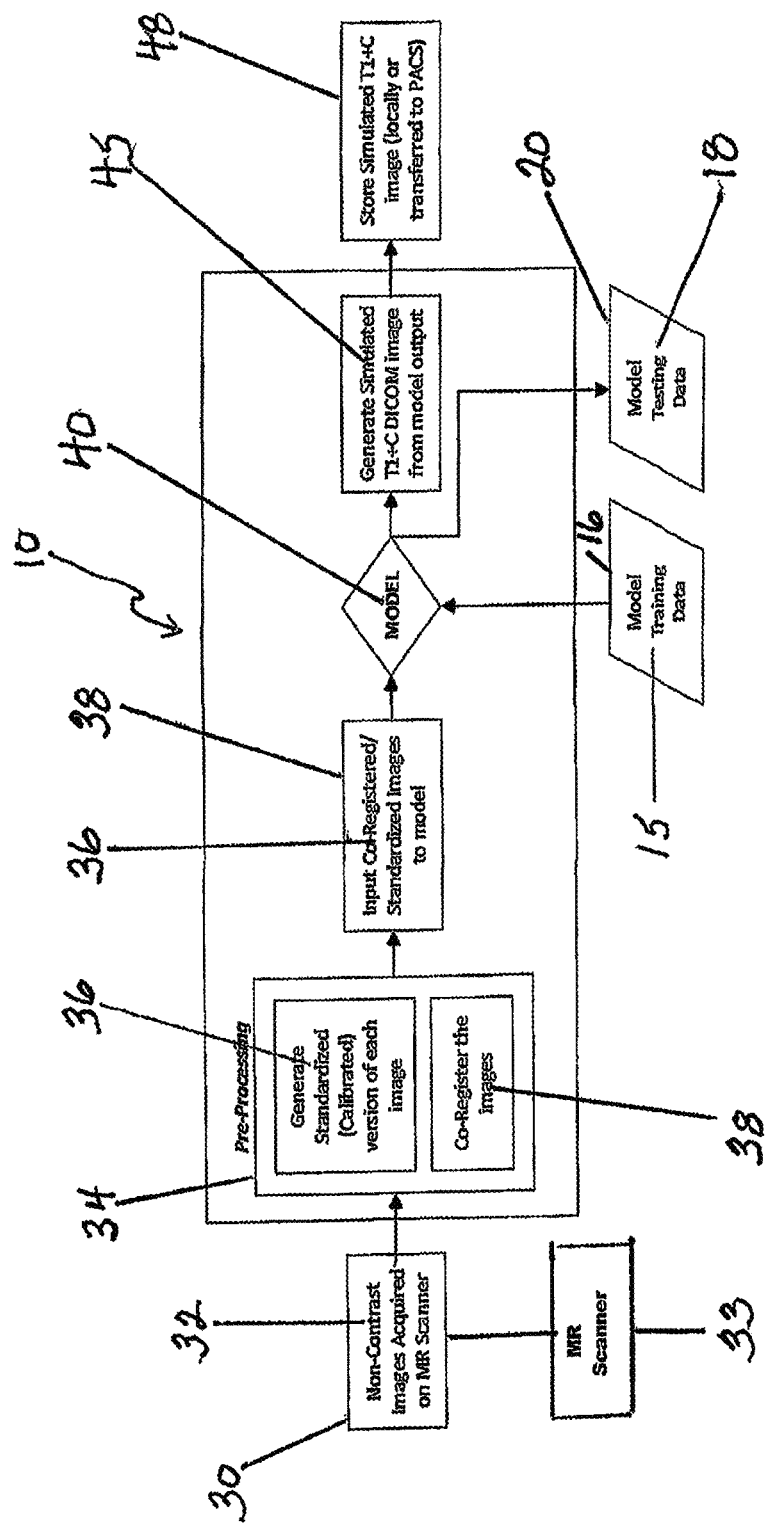
FIG. 1 is a block flow diagram illustrating the system components and the workflow steps of the method of the present invention including the steps of training and validating a processing model in accordance with an embodiment.
Figure 2:
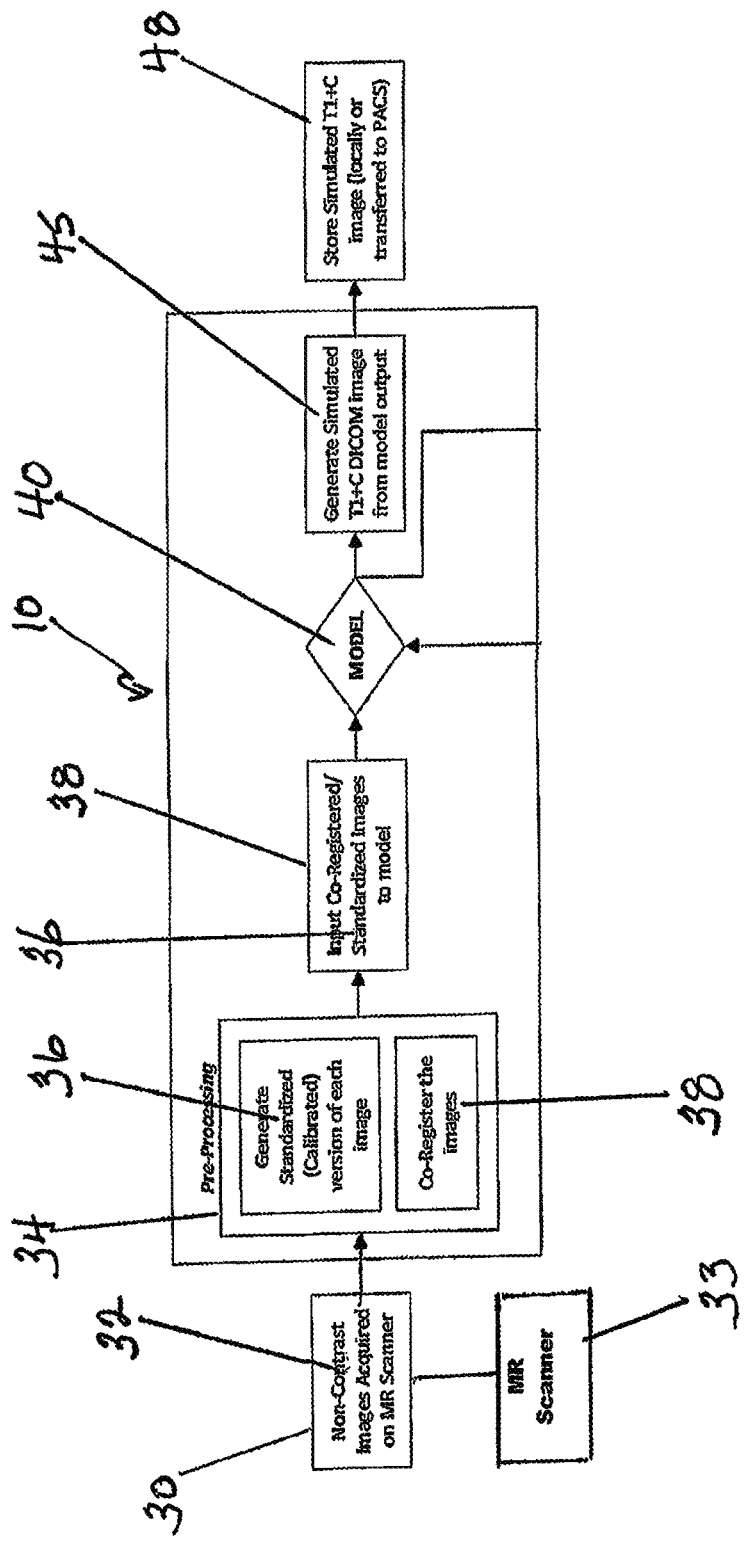
FIG. 2 is a flow diagram of the system of FIG. 1 illustrating the routine steps of the method of the present invention using a trained and validated model.
Figure 3:
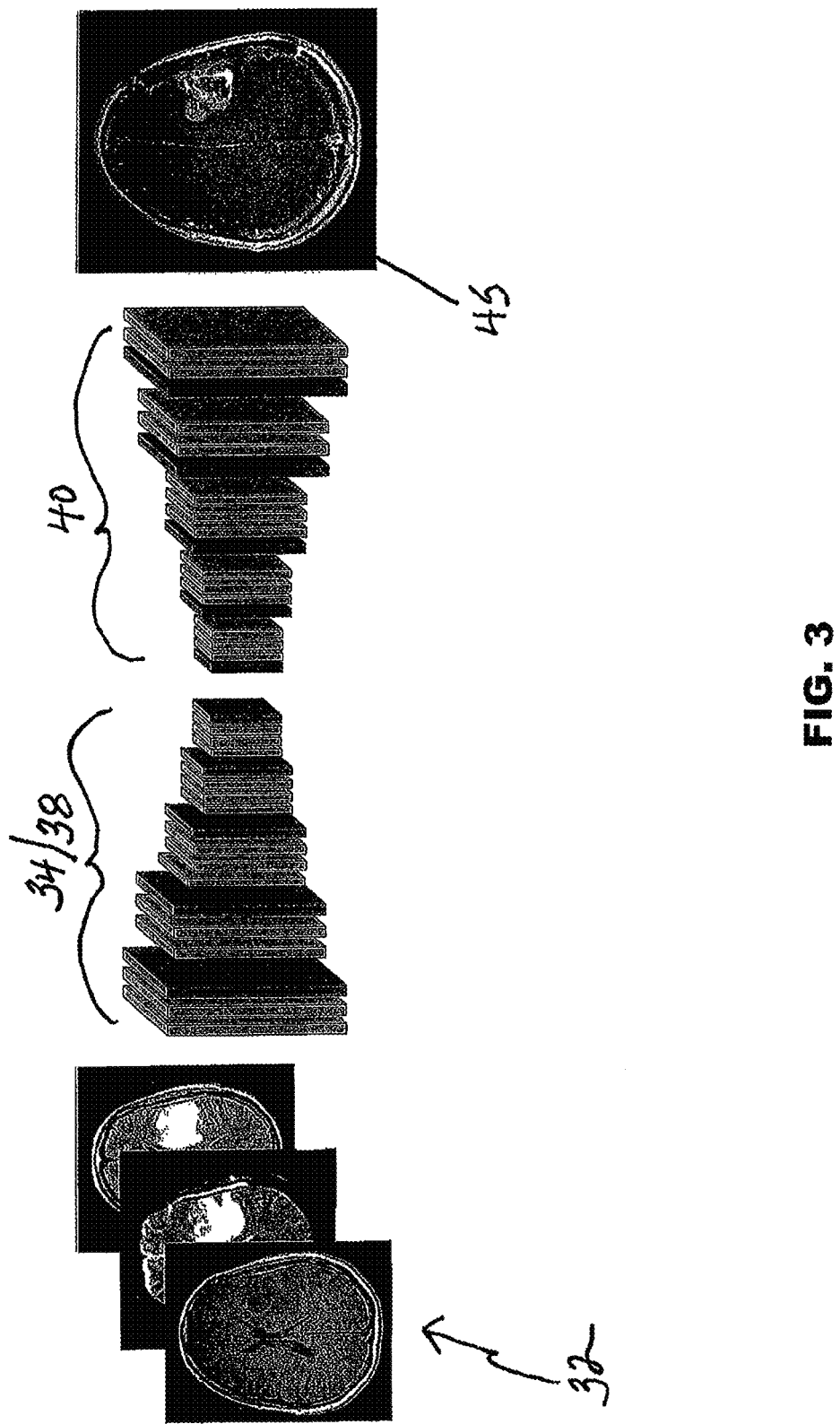
FIG. 3 is a schematic flow diagram figuratively illustrating the input of standardized reconstructed echo images of a patient, the processing thereof and the output of the model into simulated T1+C (post-contrast) weighted imaging in accordance with the flow diagrams of FIGS. 1 and 2.

Referring now to FIGS. 1 and 2, the various components of the system 10 and its inputs and output are shown in greater detail and include:

Training Data: A multi-subject collection 15 of MR images of various sequence types, by way of example and not of limitation, T1-weighted, T2-weighted, FLAIR (Fluid-Attenuated Inversion Recovery), and/or DWI (Diffusion-Weighted Imaging), collected without exogenous contrast and the corresponding post-contrast T1-weighted image for each subject in the collection and stored in a training component or module 16. The images are acquired on multiple scanners so that the collection includes images with various gradient strengths (e.g., 1.5 T, 3.0 T) collected by equipment manufactured by various vendors (e.g., Siemens, GE, Philips). The post-contrast T1-weighted images are the standards to which the testing data described below and simulated T1-weighted images are held, thus optimizing the model 30 as described below.

Testing Data: An image and data collection 18 similar to the training data but with a unique set of subjects and images, the testing data being stored in a testing component or module 20.

Training Module 16: The training component or module 16 identified above that stores the training data and communicates with the model 40 to optimize its performance and output.

Testing Module 20: The testing component or module 20 communicates with the model 40 and handles testing of the trained model to verify it meets pre-determined performance criteria.

Input Module 30: An input component or module which stores non-contrast MR images 32 for a patient acquired on a MR scanner.

Pre-Processing Module 34: The optional preprocessing module 34 receives the patient's non-contrast images 32, generates standardized (calibrated) versions 36 of each image, transfers them to an image data storage module 38 in the system 10 and co-registers (transfers) them to a radiology information system (PACS or VNA).

Simulated T1+C Model 40: A simulated T1+C model component or module 40 accepts as input registered, pre-contrast images 36 from data storage module 38 and provides post-contrast images 45 as output, which are stored in output storage module 48 or transferred to a medical picture archiving and communication system (PACS).

Machine Learning Platform By way of example and not limitation, a machine learning platform or other artificial intelligence systems may be operatively connected to the system 10 to host and run the model 40. Subcomponents within this platform include one or more machine learning toolkits and a plurality of digital file systems and computer operating systems. The training component uses the training data to adjust the tunable parameters of the simulated T1+C model so that the output images generated by the model are optimized to be analogous to the training data targets (post-contrast T1-weighted images). The testing component uses the testing data to verify that the trained simulated T1+C model meets pre-determined performance criteria. The training, testing and simulated T1+C model components use a machine learning platform to receive data, store data, perform calculations, and output data.

Process Steps

Referring again to FIG. 1, the steps of the novel method of the present invention to more clearly illustrate the inter-relationships thereof and with the various system modules.

First, the model 40 of system 10 is trained and tested using machine learning techniques to output a simulated post-contrast T1-weighted image. The training and testing steps are:

1. Collecting a plurality of non-contrast MR images of various sequence types, by way of example and not of limitation, T1-weighted, T2-weighted, FLAIR (Fluid-Attenuated Inversion Recovery), and/or DWI (Diffusion-Weighted Imaging).

2. Inputting the plurality of collected non-contrast MR images into a training module.

3. Collecting a plurality of corresponding post-contrast T1-weighted images for each subject in the collection and storing them in the training module.

4. Inputting the plurality of non-contrast MR images and corresponding post-contrast T1-weighted images into the model.

5. Using artificial intelligence techniques, by way of example and not of limitation, machine learning techniques, training the model to generate a simulated post-contrast T1-weighted image based upon the non-contrast MR images input into the model and the corresponding post-contrast T1-weighted images as the target output.

6. Testing the simulated post-contrast T1-weighted images against the corresponding post-contrast T1-weighted images previously input into the model which are the standards to which the testing data and simulated T1-weighted images are held.

7. Optimizing the model output using machine learning techniques.

Exemplary process steps using the trained system for analysis of MR images for a specific patient are as follows:

1. Acquiring pre-contrast (non-contrast) MR images of a patient for a particular study on a MR scanner.

2. Transferring (co-registering) all of the images for a particular study to a radiology information system, e.g., a picture archiving and communication system (PACS), or a VNA storage system for storage and archival purposes.

3. Transferring pre-contrast MR images for the study to the image data storage module in the system.

4. Inputting pre-contrast MR images into the model.

5. Generating simulated T1+C weighted image(s) corresponding to the pre-contrast MR input images.

6. Transferring the simulated T1+C weighted image(s) to hospital information system (PACS) to be stored and archived with other images from same study.

7. Viewing all images using viewers available with radiology information systems.

After the images are collected as described above, the following procedures are implemented for further analysis as shown in FIG. 2:

1. Receiving pre-contrast MR images in DICOM format for a patient study via network transfer (or alternatively imported into local file system).

2. Pre-processing pre-contrast MR images:

3. Co-registering images.

4. Generating standardized versions of images.

5. Passing co-registered, standardized images as inputs to model (shown as convolutional neural network in FIG. 4).

6. Generating simulated T1+C DICOM image from model output.

7. Storing simulated T1+C image (locally and/or transferred to radiology information system).

Changes may be made in the above methods and systems without departing from the scope hereof. It should be noted that the matter contained in the above description and/or shown in the accompanying figures should be interpreted as illustrative and not in a limiting sense. The following claims are intended to cover all generic and specific features described herein, as well as all statements of the scope of the present systems.

What is claimed is:

1. A system for generating a simulated post-contrast T1+C image of a patient's organ or tissue based upon non-contrast magnetic resonance images (MRI) of the organ or tissue without the injection of a contrast agent into the organ or tissue, the system comprising:
   an input module adapted to store non-contrast MR images of a patient's organ or tissue without the injection of a contrast agent into the patient's organ or tissue;
   a simulated T1+C image generating module adapted to receive each of the patient's non-contrast MR images and to generate simulated post-contrast T1+C images corresponding to each of the patient's non-contrast MR images, wherein the simulated T1+C image generating module does not receive any images of the patient's organs or tissue that include any contrast agent, the simulated T1+C image generating module further including a machine learning platform adapted to receive a plurality of non-contrast images and corresponding post-contrast images of various types including T1-weighted, T2-weighted, Fluid-Attenuated Inversion Recovery (FLAIR), and/or Diffusion-Weighted Imaging (DWI) as training data, the machine learning platform being structured and arranged to operate the simulated T1+C image generating module;
   a training module adapted to receive and communicate the training data to the machine learning platform whereby tunable parameters of the simulated T1+C image generating module are adjusted to optimize the simulated post-contrast T1+C images;
   a testing module adapted to communicate with the training module and the machine learning platform and to receive testing data whereby the simulated post-contrast T1+C images generated by the simulated T1+C image generating module are validated in accordance with pre-determined performance criteria; and
   an output storage module adapted to receive the simulated post-contrast T1+C images generated by the simulated T1+C image generating module.

2. The system of claim 1 further including a preprocessing module adapted to receive the patient's non-contrast MR images and to generate and store standardized versions of each of the patient's non-contrast MR images.

3. The system of claim 2 wherein the preprocessing module includes an image data storage module.

4. The system of claim 3 wherein the simulated T1+C image generating module is adapted to receive the standardized versions of each of the patient's non-contrast MR images.

5. A method for generating a simulated post-contrast T1+C image of a patient's organ or tissue based upon non-contrast magnetic resonance images (MRI) of the organ or tissue without the injection of a contrast agent into the organ or tissue, the method comprising:
   collecting a plurality of non-contrast MR images of a patient's organ or tissue without the injection of a contrast agent into the patient's organ or tissue;
   inputting the plurality of collected non-contrast MR images into a simulated T1+C image generating module;
   generating, by the simulated T1+C image generating module, simulated post-contrast T1+C images corresponding to each of the patient's non-contrast MR images, wherein the simulated T1+C image generating module does not receive any images of the patient's organs or, tissue that include am, contrast agent;
   collecting a plurality of non-contrast images and corresponding post-contrast images of various types including T1-weighted, T2-weighted, Fluid-Attenuated Inversion Recovery (FLAIR), and/or Diffusion-Weighted Imaging (DWI) as training data;
   storing the plurality of non-contrast images and corresponding post-contrast images in a training module;
   inputting the non-contrast images and the corresponding post-contrast images into the simulated T1+C image generating module;
   training the simulated T1+C image, generating module using the training data to adjust tunable parameters of the simulated T1+C image generating module to optimize the simulated post-contrast T1+C images;
   Validating the simulated post-contrast T1+C images in accordance with pre-determined performance criteria; and
   outputting the simulated post-contrast T1+C images.

6. The method of claim 5 wherein the plurality of non-contrast MR images includes T1-weighted, T2-weighted, Fluid-Attenuated Inversion Recovery (FLAIR), and/or Diffusion-Weighted Imaging (DWI) images.

7. The method of claim 6 wherein the step of training the simulated T1+C image generating module includes applying machine learning techniques.

8. The method of claim 7 wherein the step of validating the simulated post-contrast T1+C images includes applying machine learning techniques.

9. The method of claim 8 further including the steps of:
   acquiring non-contrast MR images of another patient for a particular study on a MR scanner;
   transferring all of the images for the particular study to a radiology information system, a picture archiving and communication system (PACS), or a Vendor Neutral Archive (VNA) storage system for storage and archival purposes;
   transferring non-contrast MR images for the study to the image data storage module in the system;
   inputting the non-contrast MR images for the study into the simulated T1+C image generating module;
   generating a simulated T1+C weighted image corresponding to each of the non-contrast MR input images; and
   viewing all images using radiology information systems viewers.

* * * * *